US00PP37681P2

(12) United States Plant Patent
Kordes et al.

(10) Patent No.: US PP37,681 P2
(45) Date of Patent: Sep. 8, 2026

(54) MINIATURE ROSE PLANT NAMED 'KORpot144'

(50) Latin Name: *Rosa hybrida*
Varietal Denomination: KORpot144

(71) Applicant: W. KORDES' SÖHNE Rosenschulen GmbH & Co KG, Klein Offenseth-Sparrieshoop (DE)

(72) Inventors: Wilhelm-Alexander Kordes, Klein Offenseth-Sparrieshoop (DE); Britta Feuerhahn, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 19/465,316

(22) Filed: Jan. 30, 2026

(51) Int. Cl.
*A01H 5/02* (2018.01)
*A01H 6/74* (2018.01)

(52) U.S. Cl.
USPC ..... Plt./119
CPC ..... *A01H 6/749* (2018.05)

(58) Field of Classification Search
USPC ..... Plt./119, 126
CPC ..... A01H 5/0222
See application file for complete search history.

(56) References Cited

U.S. PATENT DOCUMENTS

PP24,207 P2 2/2014 Kordes

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot144', is described. The new plant variety forms in abundance on a substantially continuous basis orange-colored blossoms. The growth habit is compact. Additionally, the new plant variety is particularly well suited for growing as distinctive ornamentation in the landscape.

1 Drawing Sheet

Latin name of genus and species of plant claimed: *Rosa hybrida.*

Variety denomination: 'KORpot144'.

STATEMENT REGARDING PRIOR DISCLOSURES BY THE INVENTOR

The first sale or offer for sale of the new plant variety was February 2025, on the ROSA DANICA website. The first sale or offer for sale of the new plant variety was by a joint inventor or another who obtained the new plant variety directly or indirectly from a joint inventor. No plants of the new variety have been sold in this country or anywhere in the world, nor has any disclosure of the new plant been made, more than one year prior the effective filing date of this application, and such sale or disclosure within one year was either derived directly or indirectly from a joint inventor.

BACKGROUND OF THE INVENTION

The new plant variety of miniature rose plant of the present invention was created by controlled breeding in 2021 in Offenseth-Sparrieshoop, Germany by artificial pollination wherein two parents were crossed which previously had been studied in the hope that they would contribute the desired characteristics. The female parent (i.e., the seed parent) of the new plant variety was 'KORdatiffi' (not patented). The male parent (i.e., the pollen parent) of the new plant variety was 'KORpot110' (not patented).

The parentage of the new variety can be summarized as follows:

'KORdatiffi' x 'KORpot110'

The seeds resulting from the above pollination were sown and small plants were obtained which were physically and biologically different from each other. Selective study resulted in the identification of a single plant of the new variety.

The new plant variety has been found to undergo asexual propagation at Klein Offenseth-Sparrieshoop, Germany by a number of routes such as vegetative cuttings. Asexual propagation techniques in Klein Offenseth-Sparrieshoop, Germany, such as vegetative cuttings, have shown that the characteristics of the new plant variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of miniature rose plant of the present invention possesses the following combination of characteristics:

(a) abundantly and substantially continuously forming orange-colored blossoms, and
(b) exhibiting a compact growth habit.

The new plant variety well meets the needs of the horticultural industry. It can be grown to advantage as distinctive ornamentation in parks, gardens, public areas, and residential landscapes. Accordingly, it is particularly well suited for growing in the landscape.

The new plant variety can be readily distinguished from its ancestors. More specifically, the new plant variety displays a smaller flower size compared to the 'KORdatiffi' variety (i.e., the seed parent). Additionally, the new plant variety displays a more upright growth habit compared to the 'KORpot110' variety (i.e., the pollen parent). Moreover, the new plant variety can be readily distinguished from non-parental related similar varieties. For example, the new plant variety displays fewer petals and a stronger orange flower color compared to the 'KORpot021' variety (U.S. Plant Pat. No. 24,207).

The new variety has been named the 'KORpot144' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new plant variety. The illustrated rose plant of the new variety was approximately twelve weeks of age and was grown indoors on its own roots in a 10.5 cm container in Klein Offenseth-Sparrieshoop Germany on Dec. 19, 2024.

Drawing — illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms. The R.H.S. Colour Chart designation used herein represents the closest color observed on the majority of the specified botanical features. The description is based on a two-year-old specimen of the new plant variety, observed during May 2026, while growing on its own roots in a three-gallon container in a greenhouse in Cochranville, Pennsylvania.

Botanical classification: *Rosa hybrida* cultivar 'KORpot144'.

Commercial classification: Miniature Rose.

Plant:

*Habit*.—Compact.

*Height*.—Approximately 39.0 cm on average from the top of the soil plane.

*Width*.—Approximately 30.0 cm on average.

Branches:

*Stem color*.—Old wood: Green Group 137C. — young stems: Green Group 143C suffused throughout with Greyed-Orange Group 176B.

*Length*.—Main stems: approximately 39.0 cm on average. — secondary stems: approximately 30.0 cm on average.

*Diameter*.—Main stems: approximately 8.0 mm on average. — secondary stems: approximately 4.0 mm on average.

*Texture*.—Smooth.

*Prickles*.—Amount: very few; 0 to 1 prickle per internode. — young prickles: length is approximately 5.0 mm on average; width is approximately 4.0 mm on average at point of attachment; and color is Greyed-Purple Group 183A. — old prickles: length is approximately 5.0 mm on average; width is approximately 4.0 mm on average at point of attachment; and color is Grey-Brown Group N199B.

Leaflets:

*Number*.—3, 5, and 7.

*Shape*.—Ovate; apex is acute to acuminate; and base is cuneate.

*Arrangement*.—Odd-pinnate.

*Margin*.—Serrate.

*Undulation*.—Moderate.

*Texture*.—Upper surface: smooth. — under surface: smooth.

*Venation pattern*.—Reticulate.

*Size*.—Terminal leaflet: length is approximately 5.2 cm on average; width is approximately 3.5 cm on average. — lower leaflets: length is typically 3.5 cm to 4.0 cm; width is typically 2.0 cm to 2.8 cm. — 5-Leaflet leaf: length is approximately 12.5 cm on average; width is approximately 8.5 cm on average.

Foliage:

*Young foliage*.—Upper surface color: Green Group NN137B with a leaf margin of Greyed-Purple Group 187A with no visible venation. — under surface color: Yellow-Green Group 147B with venation of Greyed-Purple Group 187A.

*Old foliage*.—Upper surface color: Green Group NN137B with no visible venation. — under surface color: Yellow-Green Group 147B with no visible venation.

*Petiole*.—Texture: upper surface is hispid; under surface is minute prickles. — length: approximately 2.5 cm on average. — width: approximately 1.0 mm on average. — upper surface color: Green Group 137B. — under surface color: Green Group 137D.

*Rachis*.—Length: approximately 2.0 cm on average. — width: approximately 1.0 mm on average. — upper surface color: Green Group 137B. — under surface color: Yellow-Green Group 144A. — texture: upper surface is hispid; under surface is smooth.

*Stipules*.—Length: approximately 2.5 cm on average. — width: approximately 4.0 mm on average. — margin: entire to erose. — upper surface color: Green Group 143A. — lower surface color: Green Group 143B.

Inflorescence:

*Number of flowers*.—About 12 to 15 blooms on average on a plant at once.

*Number of blossoms per stem or in a cluster*.—Typically 1 bloom per stem on average.

*Peduncle*.—Color: Green Group 143C overlayed with Greyed-Orange Group 176A throughout. — diameter: approximately 3.0 mm on average. — length: approximately 5.5 cm on average. — surface texture: smooth.

*Sepals*.—Number: 5. — upper surface color and texture: Yellow-Green Group 147C, covered in short pubescence. — under surface color and texture: Green Group 143A, puberulent. — size: length is approximately 4.5 cm on average; width is approximately 1.0 cm on average. — margin: entire with extensions on most sepals measuring approximately 1.0 cm in length and 1.0 mm in width on average. — shape: ovate. — apex: acute to aristate. — base: truncate as it joins the receptacle.

*Buds*.—Shape: ovoid. — size: length is approximately 3.0 cm on average; width is approximately 2.0 cm on average. — color (when opening): Greyed-Purple Group 184A.

*Flower*.—Form: double, cuplike. — profile: concave as it opens, and then outer petals are convex as the bloom ages and opens further. — diameter: approximately 9.0 cm on average. — height: approximately 4.0 cm on average. — duration: on the plant approximately 10 to 12 days. — petal color when first and fully opened: ombre with darkest petals to the outside, lightest to the center; inner petals, upper surface: Orange-Red Group 35A with medium basal spot of Yellow-Orange Group 17A; inner petals, under surface: Red Group 37A with medium basal spot of Yellow-Orange Group 17A; outer petals, upper surface: Red Group N45D with medium basal spot of Yellow-Orange Group 17A; outer petals, under surface: Red Group N45D with no visible basal spot. — petal color at end of bloom: inner petals, upper surface: Orange-Red Group 34D with Yellow-Orange Group 16A basal spot; inner petals, under surface: Orange-Red Group N34C with Yellow-Orange Group 16A basal spot; outer petals, upper surface: Red Group 51A with Yellow-Orange Group 15A basal spot; outer petals, under surface: Red Group 51A with Yellow-Orange Group 15A basal spot. — petals reflex one by one: yes.

*Fragrance*.—No noticeable scent.

*Petal*.—Number: 70 to 80 on average. — drop: average. — length: typically 3.5 cm to 5.0 cm. — width: typically 2.3 cm to 4.5 cm. — overall shape: broadly obovate. — margin: entire with moderate undulation. — apex shape: rounded. — base shape: cuneate. — texture: upper surface is smooth; under surface is smooth.

*Petaloids*.—Number: approximately 11 on average. — length: typically 2.0 cm to 3.0 cm. — width: typically 5.0 mm to 1.0 cm. — color: upper surface is Orange-Red Group 35A with a medium basal spot of Yellow-Orange Group 21A; under surface is Orange-Red Group 35A with a medium basal spot of Yellow-Orange Group 21A. — texture: upper surface is smooth; under surface is smooth. — margin: entire with moderate undulation. — shape: obovate. — apex: obovate. — base: linear.

*Stamen*.—Number: approximately 115. — anthers: number is approximately 115; color is Yellow-Orange Group 16A; length is approximately 3.0 mm on average; width is approximately 1.0 mm, and shape is oval. — filaments: length is approximately 4.0 mm on average and color is Yellow-Orange Group 19A.

*Pistils*.—Arrangement: fused at the base, separate at apex. — number: approximately 216. — style: length is approximately 6.0 mm on average and color is Yellow Group 11D. — stigma: diameter is approximately 1.0 mm on average; shape is fan shaped; color is Yellow Group 11A.

*Receptacle*.—Diameter: approximately 1.3 cm on average. — depth: approximately 1.0 cm on average. — shape: urn shaped. — color: Yellow-Green Group 144B. — surface texture: smooth.

*Pollen*.—None observed to date.

*Hips/seed*.—None observed to date.

DEVELOPMENT:

*Vegetation*.—Glossy and dark green.

*Blossoming*.—Abundant and substantially continuous from spring through frost; typically, in bloom outdoors from May to November in Southeastern Pennsylvania.

*Resistance to diseases*.—Good resistance to powdery mildew (*Sphaerotheca pannosa*).

*Hardiness*.—Unknown.

The new 'KORpot144' variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of miniature rose plant named 'KORpot144' characterized by the following combination of characteristics:

(a) abundantly and substantially continuously forming orange-colored blossoms, and (b) exhibiting a compact growth habit;

substantially as herein shown and described.

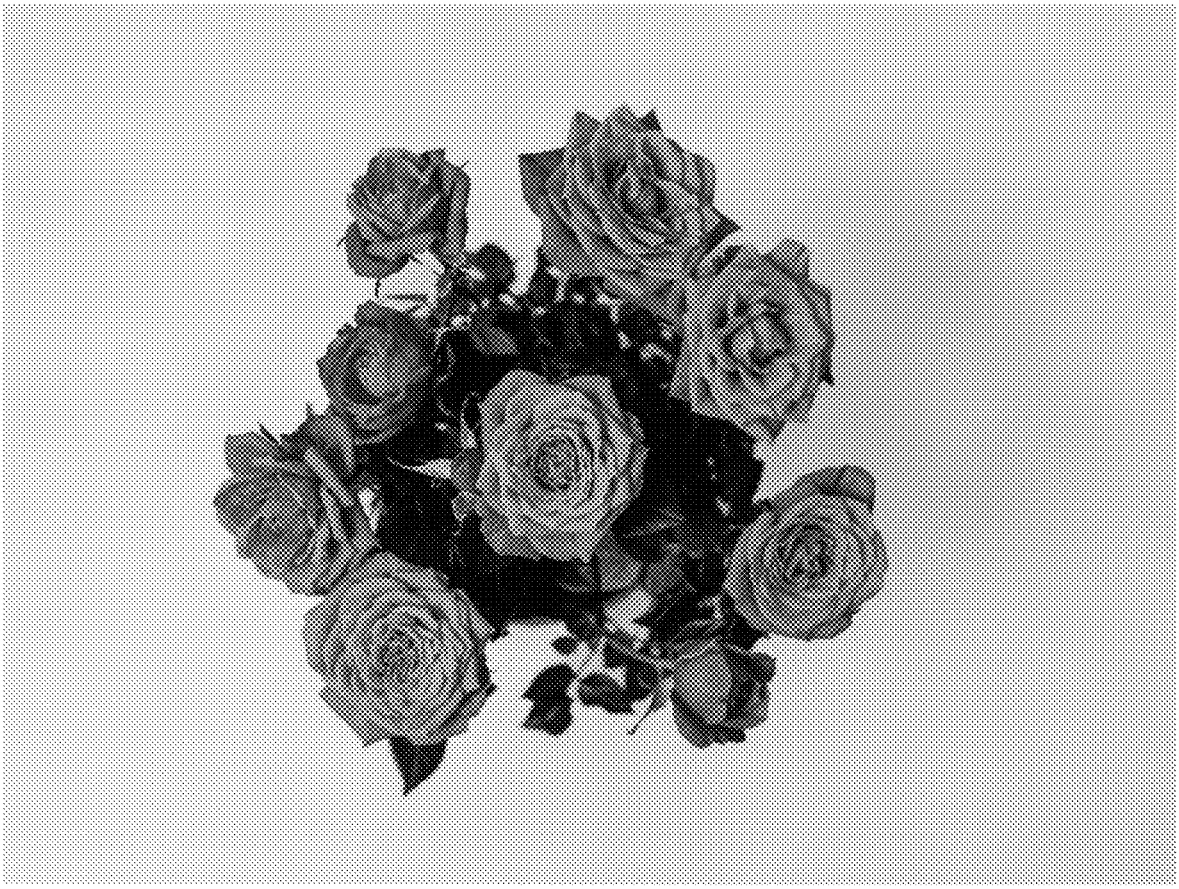

* * * * *